US007839507B2

(12) United States Patent
Gunstream et al.

(10) Patent No.: US 7,839,507 B2
(45) Date of Patent: Nov. 23, 2010

(54) MINIMIZING EFFECTS OF DYE CROSSTALK

(75) Inventors: Stephen J. Gunstream, San Francisco, CA (US); David C. Woo, Foster City, CA (US); John P. Bodeau, San Mateo, CA (US); Mark A. McCoy, Foster City, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 564 days.

(21) Appl. No.: 11/770,443

(22) Filed: Jun. 28, 2007

(65) Prior Publication Data

US 2008/0018898 A1 Jan. 24, 2008

Related U.S. Application Data

(60) Provisional application No. 60/806,061, filed on Jun. 28, 2006.

(51) Int. Cl.
*G01N 21/25* (2006.01)
(52) U.S. Cl. ...................................... 356/417
(58) Field of Classification Search .................. 356/417
See application file for complete search history.

(56) References Cited

U.S. PATENT DOCUMENTS 6,333,501 B1    12/2001  LaBrenz
6,863,791 B1    3/2005   Liu et al.
7,035,739 B2    4/2006   Schadt et al.
7,209,836 B1 *  4/2007   Schermer et al. .............. 702/19
2004/0259260 A1 * 12/2004  Gunstream et al. ....... 422/82.05
2007/0100569 A1 * 5/2007   DeSimas et al. .............. 702/85

OTHER PUBLICATIONS

Yin et al. "Automatic matrix determination in four dye fluorescence-based DNA sequencing", 1996, Eletrophoresis, vol. 17, pp. 1143-1150.*
Lewin et al., Quantiative DNA Methylation Anaylsis Based on Four-Dye Trace Data from Direct Sequencing of PCR Amplificates, Bioinformatics, vol. 20, pp. 3005-3012, 2004.
International Search Report for Int'l application No. PCT/US07/72383 dated Jul. 29, 2008, along with Written Opinion of the International Searching Authority.

* cited by examiner

*Primary Examiner*—Kara E Geisel

(57) ABSTRACT

Methods and systems for processing signals to minimize the effects of dye crosstalk. Deconvolution of multiplexed dye signals can include corrections for residual error determined from experimental measurements. Residual error corrections can account for reaction or assay specific factors and modify the subsequent filtering of signals. Correction values can be determined for specific dye-probe conjugates to minimize dye crosstalk and may be combined with residual error correction to further minimize errors in spectral deconvolution. Apparatus, systems, and computer-readable media can process signals and modify filters based on values obtained using the methods.

33 Claims, 12 Drawing Sheets

|  | | FAM | VIC | ROX |
|---|---|---|---|---|
| Original Calibration | A | 1.0000 | 0.0835 | 0.0010 |
|  | B | 0.6532 | 1.0000 | 0.0147 |
|  | C | 0.2063 | 0.3735 | 0.2035 |
|  | D | 0.0862 | 0.1506 | 1.0000 |

← 805

|  | | FAM | VIC | ROX |
|---|---|---|---|---|
| Corrected Calibration | A | 1.0000 | 0.0835 | 0.0010 |
|  | B | 0.6180 | 1.0000 | 0.0139 |
|  | C | 0.2063 | 0.3735 | 0.2035 |
|  | D | 0.0862 | 0.1506 | 1.0000 |

MINIMIZING EFFECTS OF DYE CROSSTALK

CROSS-REFERENCE TO RELATED APPLICATIONS

This application claims the benefit of U.S. Provisional Application No. 60/806,061, filed on Jun. 28, 2006. The disclosure of the above application is incorporated herein by reference.

All literature and similar materials cited in this application, including but not limited to, patents, patent applications, articles, books, treatises, and internet web pages, regardless of the format of such literature and similar materials, are expressly incorporated by reference in their entirety for any purpose. In the event that one or more of the incorporated literature and similar materials differs from or contradicts this application, including but not limited to defined terms, term usage, described techniques, or the like, this application controls.

INTRODUCTION

A reporter dye may be used to detect a biochemical or biophysical event by measuring the dye spectrum to detect presence or absence of the dye or relative change in a dye signal. For example, dyes are used to ascertain binding of a dye-probe conjugate to a target, amplification of dye signal due to product formation, such as a PCR amplicon, as well as measuring the absence of binding or decrease in product. Economy and efficiency needs have led to the multiplexing of dyes, where multiple dyes are used in the same reaction or assay, and may further include performing target and reference reactions in the same volume, tube, or well. Multiplexing offers higher throughput, more efficient use of samples, and a reduction in reagent use and cost.

Multiplexing dyes is complicated by overlap between dye spectra. As a result, signal processing methods are used to determine the contribution of each dye component. A process called multicomponenting may be used to distinguish individual reporter dyes. Multicomponenting includes a mathematical algorithm that uses pure dye reference spectra to calculate the contribution of each dye in a complex experimental spectrum. As a result, individual dye components can be deconvoluted from complex spectra; however, crosstalk between dye spectra can lead to errors in signal processing.

SUMMARY

The present teachings relate to processing data signals and include methods and systems for minimizing spectral crosstalk. In some embodiments, methods can include providing for a plurality of filters, where each filter is configured to capture a different set of spectral wavelengths. Methods may also include determining a residual error for each filter during dye amplification and modifying the spectral deconvolution matrix based on the residual error. Methods may further include filtering subsequent signals associated with the modified at least one filter.

In some embodiments, the present teachings include systems for minimizing spectral crosstalk. Systems can have a detector configured to detect a plurality of signals from a sample and a signal processor configured to filter the plurality of signals. The signal processor includes a plurality of filters, each filter associated with a dye and a plurality of matrices. Each matrix is associated with a respective filter, where each matrix is initially configured with an expected response. The system may also include a residual error correction ("REC") module configured to monitor for residual errors of the plurality of filters during a dye amplification phase and to modify the associated matrices of the plurality of filters to minimize the residual error.

In some embodiments, methods for processing signals include providing a first dye signal based on measurement of a first dye and providing at least one probe signal based on measurement of the first dye conjugated to a first probe. The change between the first dye signal and the at least one probe signal is processed to provide a first correction value particular to the first dye conjugated to the first probe. Such methods may further include deconvolution of a multiplexed signal, which includes a component from the first probe, by using the first correction value.

In some embodiments, methods for correcting spectral shift based on dye-probe conjugation include adjusting a probe measurement using a first correction value as determined by the present teachings. In addition, these methods may include deconvoluting a multiplexed probe measurement where the multiplexed probe measurement includes components from a plurality of different probes. Deconvoluting may also use a plurality of correction values as determined by methods of the present teachings.

The present teachings afford several benefits including reducing or substantially eliminating error due to spectral crosstalk Ability to measure and account for assay and dye specific errors can increase the accuracy of data obtained by multicomponenting of multiplexed assays. For example, minimizing error and spectral crosstalk within instrument calibration, detection systems, and signal processing methods can allow more accurate data collection. In some embodiments, higher-performance multiplexed analyses are possible using the present technology. Better spectral deconvolution can be achieved which, for example, reduces false positive Ct assignments in multiplexed real-time PCR. Improved spectral deconvolution also enables greater accuracy and precision in processing dye signals. Such improvements can provide more accurate baselining in determining and assigning Ct values. These and other features of the present teachings are set forth herein.

BRIEF DESCRIPTION OF THE DRAWINGS

The skilled artisan will understand that the drawings, described herein, are for illustration purposes only The drawings are not intended to limit the scope of the present teachings in any way.

FIG. 8 depicts exemplary original and corrected calibration values for FAM, VIC and ROX dyes;

DESCRIPTION

Figure 1:
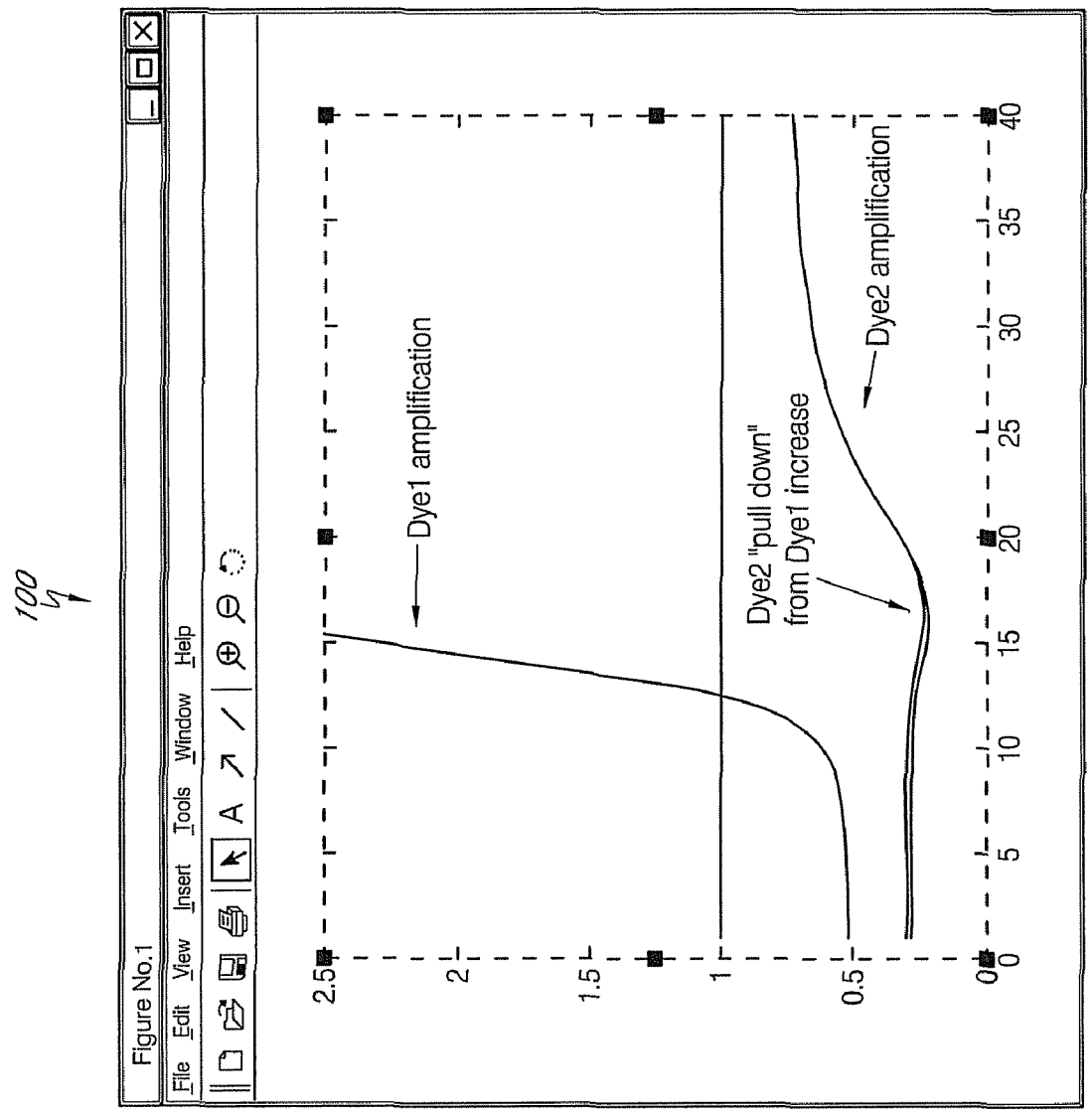
FIG. 1 illustrates the amplification spectra and response curve for two dyes showing the pull-up/pull down phenomenon.

The following description of some embodiments is merely exemplary in nature and is in no way intended to limit the present teachings, applications, or uses. Although the present teachings will be discussed in some embodiments as relating to minimizing spectral crosstalk in multiplexed real-time PCR, such discussion should not be regarded as limiting the present teaching to only such applications The section headings and sub-headings used herein are for general organizational purposes only and are not to be construed as limiting the subject matter described in any way.

Multiplexing reporter dyes is complicated by overlap between dye spectra. As a result, signal processing methods are used to determine the contribution of each dye component. A process called multicomponenting may be used to distinguish individual reporter dyes. Multicomponenting can include a mathematical algorithm that uses pure dye reference spectra to calculate the contribution of each dye in a complex experimental spectrum. For example, multiplex PCR makes it possible to amplify and detect one or more target amplicons and an endogenous control amplicon in the same reaction. The complex spectrum resulting therefrom is processed using matrix deconvolution to determine the relative individual dye signals. Deconvolution is necessary in order to accurately distinguish between dyes whose spectra may overlap. Inaccuracies between a pure dye matrix and the spectra of each dye during amplification can cause a "pull-up" or "pull-down" in measured signal, a circumstance where as one dye increases in intensity, errors in deconvolution cause a spectrally adjacent dye's calculated signal to decrease or increase. Another scenario for spectral crosstalk is that dyes are typically contained within adjacent reservoirs or wells on a multiwell plate. Neighboring wells may relate to spatial crosstalk in which dye signal from one well actually increases the dye signal in another well. Dye signal bleed and scatter may therefore introduce additional error.

Inaccuracies in the pure dye matrix can be caused by a number of factors, such as pH, temperature, buffer differences, and/or dye configuration changes. In order to minimize these inaccuracies, a spectral dye buffer similar to the buffer used in the assay or reaction conditions is typically used for each pure dye calibration. Differences in the pure dye calibration plate and the actual reaction mix can generate false positives, false negatives, or incorrect threshold cycle (Ct) values, where Ct value may be defined as the PCR cycle at which an increase of fluorescence is detected. Moreover, differences in batch lots of both the assay or reaction mix and the spectral dye mix make it difficult to obtain a "perfect" calibration.

A situation in which the spectra measured in a calibration run differ slightly from the spectra exhibited by the products of the target reaction may lead to systematic error in subsequent production-run data processing. Typically, a calibration matrix may be obtained from a calibration plate and used in a first step of processing the raw fluorescence-intensity data in a procedure known as multicomponenting. For example, an instrument may collect fluorescence intensity values of multiple dyes during each instance of measurement over several predefined ranges of light wavelength (i.e., virtual filters). The raw-data electropherogram constitutes the sequential collection of all such measurements made by the system during the run. Multicomponenting may then be used to distinguish the individual reporter dyes. Spectral calibration methods and systems, including use of calibration plates, are further described in U.S. Patent Application Publication No. 2007/0100569 to DeSimas et al., U.S. Pat. No. 6,333,501 to LaBrenz, and U.S. Patent Application Publication No. 2005/0059046 to LaBrenz et al., which are all incorporated herein by reference.

Multicomponenting may be accomplished using a mathematical algorithm that uses pure dye reference spectra to calculate the contribution of each dye in a complex experimental spectrum, and may comprise a matrix multiplication of each measurement vector by the inverse of the calibration matrix. If the number of virtual filters collected from the instrument is greater than the number of dye signals to be computed, the pseudo-inverse of the calibration matrix may be used in place of the ordinary inverse. This process is intended to transform the dye intensity data from the vector space of relative intensity in each of the virtual filters, to the vector space of relative dye-label concentrations in a way that is mathematically optimal in a least mean-squares sense.

The manifestation of calibration error in the multicomponenting process is a phenomenon known as "pull-up" or "pull-down" (PU/PD) in the transformed intensity data. In a region of an electropherogram where there exists a peak in a single dye-labeled component, PU/PD can exhibit a false peak or "negative peak" in one or more of the alternate dye signals. For example, given that a peak in one of the dye signals of the transformed data otherwise corresponds to detection of a particular dye-probe conjugate, positive peaks in alternate colors (i.e., an alternate dye-labeled species, such as one or more additional dye-probe conjugates) may be interpreted in the subsequent analysis as representing a low-level presence of the corresponding dye-labeled component, when in fact there is none. This type of error can, therefore, introduce a signal indicating the false presence of another dye-labeled species, as shown in FIG. 1, which depicts a "pull-down" of one dye.

As shown in FIG. 1, the signal strength of dye 1 and dye 2 are plotted on a graph 100, where the abscissa is the number of cycles and the ordinate is the signal strength of the dye amplification. Dye 1 begins increasing in signal strength from approximately cycle 11 to 15. Dye 2, if alone, would begin to show signal strength increases at about approximately at cycle 15. However, because the amplification of dye 1, the signal of dye 2 is pulled-down or masked by the dye 1 amplification between cycles 16-20. From cycle 20, the signal from dye 2 becomes more prominent. In this case, for example, the Ct value of an amplicon relating to dye 2 can be erroneously shifted to a later cycle.

Two dyes that show significant signal in neighboring channels include, for example, the VIC and Ned dyes. These two dyes have more than 25% of the total signal in the neighboring filter, as opposed to other dyes such as FAM, ROX, and Cy5 which typically have less than 10% of the total signal in neighboring filters. In the case of VIC and Ned, these dyes are particularly susceptible to spectral crosstalk. Consequently, a 1 nm different between the calibration and amplification spectra may result in up to 5% "pull up" or "pull down" relative to the increasing dye signal.

Should miscalibration manifest itself as pull-down (negative peaks), heuristic algorithms typically used to determine the baseline (background) signal in each dye/color channel as a function of time may be adversely affected. This can then lead to further problems in the subsequent processing of the data, such as the appearance of additional false peaks due to band-pass filtering or deconvolution of elevated baseline regions, etc. Depending upon the quality of the data being processed, a low level of false peaks introduced by spectral miscalibration error may drastically lower the effective signal-to-noise ratio of the electropherogram measurements.

If low-level peaks cannot otherwise be classified as real peaks or false ones, they will effectively define a threshold of true peak detection. Therefore, applications demanding a large dynamic range of detection may be adversely affected or rendered infeasible if the spectral calibration cannot be performed accurately. A good example of such an application is sequencing for polymorphism (heterozygote) detection. In such an application, heterozygous positions in a sequence are manifest as truly (or nearly) overlapping peaks in the electropherogram. Certain protocols, such as when pooling patient samples, demand a low threshold of detection and correspondingly large dynamic range.

In some embodiments, the present teachings relate to methods of reducing spectral crosstalk. Embodiments may use residual error to correct for spectral crosstalk. The residual error is the error from an actual reaction or assay, such as PCR, that can be used to determine a more accurate pure dye signal and corresponding matrix for deconvolution. For example, residual errors arise for each dye filter because deconvolution is not a perfect solution. Embodiments of the present teachings monitor the changes of the residual errors during amplification and make it possible to quantify the error in the pure dye matrix, and subsequently correct for the error.

In some embodiments, a method for processing signals employs one or more filters where each filter is configured to process the signal from an associated dye. During amplification of dye signal, a residual error is determined for one or more of the filters, whereupon the filter is subsequently modified based on the residual error. Consequently, subsequent signals associated with the modified filter are filtered by the modified filter. Determining residual error may also include monitoring the response curve of one or more filters for a selected sample and ascertaining at least one error between the response curve and an expected response curve for each filter.

In various embodiments, a filter may include a diffraction grating and/or a prism. In some embodiments, a diffration grating or a prism may be used in place of a filter. For example, methods and systems of the present teachings may include a diffraction grating or a prism that is modified based on the residual error and/or modified based on a correction value particular to a dye conjugated to a probe.

In some embodiments, a residual error correction ("REC") module can be configured to determine the residual error for a selected dye during signal amplification The REC module can modify the pure dye matrix associated with the selected dye to reduce the residual error to become substantially flat. The REC module can then use the modified pure dye matrix to process subsequent runs.

Figure 2A:
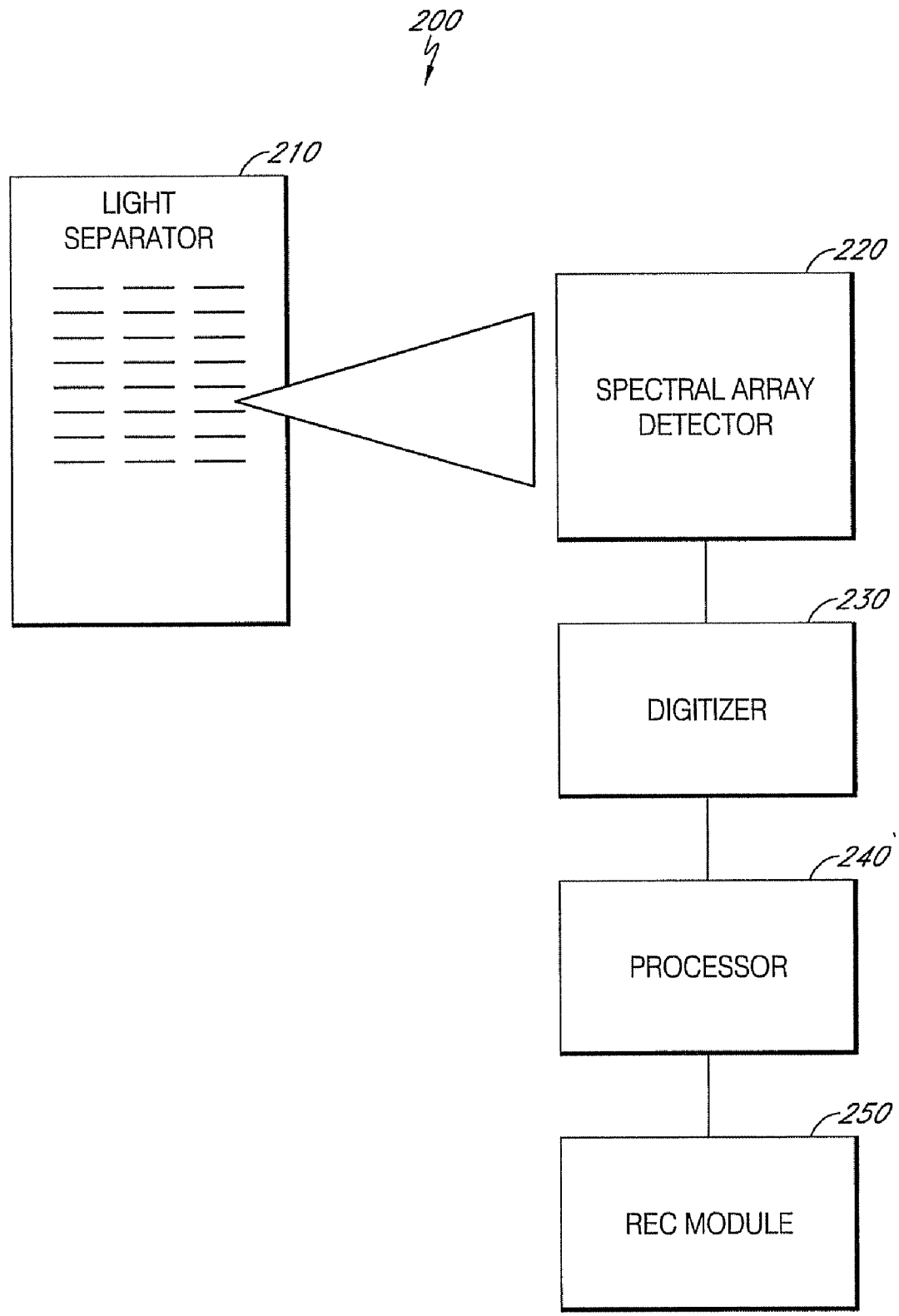
FIG. 2A illustrates a block diagram of an exemplary system constructed according to the present teachings.

FIG. 2A is an exemplary system 200 constructed according to an embodiment of the present teachings. The system 200 includes a light separator 210, a spectral array detector 220, a digitizer 230, and a processor 240. The light separator 210 spatially separates multiple spectrally-distinguishable species, such as multiple dyes. The light separator 210 may include a spectrograph, a diffraction grating, a prism, a beam splitter in combination with optical filters, or similar elements.

Figure 2B:
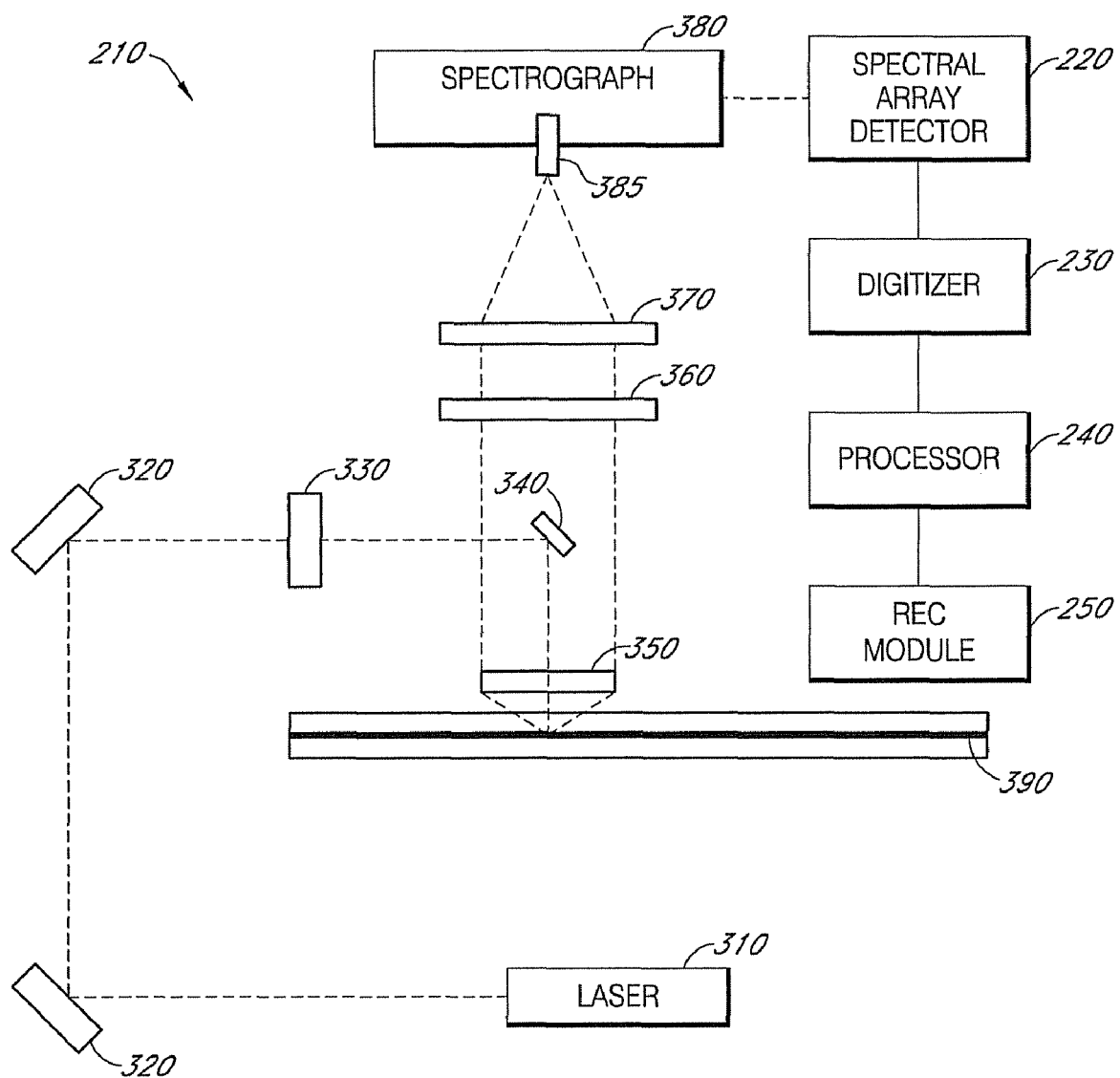
FIG. 2B illustrates a block diagram of the light separator shown in FIG. 2A.

FIG. 2B is a diagram of the light separator 210 in an implementation consistent with the present teachings. The light separator 210 includes a laser 310, a pair of mirrors 320, lenses 330, mirror 340, lens 350, filter 360, lens 370, and spectrograph 380. The laser 310 is an excitation light source, such as an argon ion laser, that may emit a polarized light beam. The mirrors 320 may be adjustably mounted to direct the laser light beam to the desired location. The lenses 330 may include telescope lenses that reduce the diameter of the light beam reflected by the mirrors 320 and present the reduced light beam to the mirror 340. The mirror 340 may include a bending mirror that directs the light to a sample 390. Samples may include, but are not limited to, experimental samples and/or controls contained within a volume, wells on a multiwell plate, such as a PCR reaction plate, a region of an electrophoresis medium, such as a capillary electrophoresis system or an aqueous gel, or any volume, reservoir, or reaction containing one or more dyes or dye-probe conjugates.

The lens 350 may include an aspheric collection lens that collects the light emitted from the laser-excited medium 390 and collimates the light in the direction of the filter 360, bypassing mirror 340. The filter 360 may include a laser rejection filter that reduces the level of scattered laser light transmitted to the lens 370. The lens 370 may include a plano-convex lens that focuses the filtered light to the spectrograph 380. The spectrograph 380 may include a slit 385 that receives the light from the lens 370 and a blaze grating (not shown) that separates the light into its spectral components. The spectrograph 380 outputs the light to the spectral array detector 220.

Returning to FIG. 2A, the spectral array detector 220 includes an optical detector that can simultaneously detect and identify an intensity of multiple wavelengths of light. The spectral array detector 220 may include an array of detector elements sensitive to light radiation, such as a diode array, a charged coupled device (CCD), a charge induction device (CID), an array of photomultiplier tubes, etc. The output of the spectral array detector 220 is light intensity as a function of array location, such that the array location can be directly related to the wavelength of the light impinging on that location.

The digitizer 230 receives the output from the spectral array detector 220, digitizes it, and presents it to the processor 240. The digitizer 230 may include an analog-to-digital converter or a similar device. The processor 240 operates upon the digitized output of the spectral array detector 220 to perform spectral calibration. The processor 240 may include any conventional processor, microprocessor, digital signal processor, or computer capable of executing instructions. The processor 240 may also include memory devices, such as a RAM or another dynamic storage device, a ROM or another type of static storage device, and/or some type of magnetic or optical recording medium and its corresponding drive; input devices, such as a keyboard and a mouse; output devices, such as a monitor and a printer; and communication device(s) to permit communication with other devices and systems over any communication medium.

The processor 240 operates upon data resulting from an analytical separation of spectrally-distinguishable molecular species to perform spectral calibration. The processor 240 performs the spectral calibration by executing sequences of instructions contained in a memory. Such instructions may be read into the memory from another computer-readable medium or from another device over a communications medium. Execution of the sequences of instructions contained in the memory causes the processor 240 to perform the methods of the present teachings. Alternatively, hardwired circuitry may be used in place of or in combination with software instructions to implement the present teachings. Thus, embodiments are not limited to any specific combination of hardware circuitry and software.

The processor 240 uses the data from the spectral array detector 220 to generate an electropherogram Y, with a dimension of $n_t \times n_b$, which is a matrix of intensity as a function of spectral bin number (ranging from 1 to $n_b$) and time of detection (ranging from 1 to $n_t$). The column vectors of the electropherogram are composed of intensity values for a given detector element, or a sum of intensity values over a series of detector elements, at different times, and the row vectors are composed of intensity values for a given time measured at different detector elements or a sum of intensity values measured over a series of detector elements. The method used to identify regions in the electropherogram Y that have a spectral response characteristic of one or two spectrally-distinguishable molecular species depends on the type of data that is expected.

If the data includes regions of pure component spectral responses, a Type I method may be used as described in U.S. Pat. No. 6,333,501 to LaBrenz. This type of data could be expected in situations in which the analytical separation process results in at least one isolated peak representing each of the distinct pure-component molecular species (e.g., pure dye-probe conjugate), such as a DNA fragment, labeled with a different one of the dyes. The Type I data need not, however, consist entirely of isolated pure components, but may also contain regions of mixtures (i.e., spatially-indistinguishable peaks).

Alternatively, if the data does not include such regions, but includes regions of binary component spectral responses, then a Type II method may be used as described in U.S. Pat. No. 6,333,501 to LaBrenz. This type of data could be expected in situations in which the analytical separation process is unable to provide spatially-distinguished peaks in which each peak consists of a pure component molecular species, and can only provide regions resulting from the combined emission from two dyes (i.e., a binary mixture region). Typically, as in DNA sequencing applications, the peaks constituting the separate components of the mixture are out-of-phase to some extent in the time domain of the electropherogram. The Type II data may also be characterized by some regions of isolated (pure) components, but in such a way that it is difficult to reliably distinguish between these and other (similar) regions containing low levels of "contamination" from another species.

Both Type I and II methods are methods of Factor Analysis (FA) or Blind Separation of Sources (BSS). Each method operates well with particular types of data. The goal of both, however, is the same; namely, to extract the source or basis functions representing the independent components present in a mixture without any specific prior knowledge of their shape (hence "blind" in BSS). In the present context, the physical components include distinct dyes and the basis functions include their individual fluorescence spectra, such as relative emission intensity versus wavelength.

Another term that is frequently encountered in this context is mixture analysis (i.e., the output signals are produced by an instantaneous linear mixture of the source signals). As general methodologies, FA and/or BSS have been applied in many different contexts, including gas chromatography, mass spectrometry, magnetic resonance spectroscopy, as well as other more distantly-related applications in signal processing and statistical analysis.

These methods are deterministic in the sense that they are designed to isolate and classify regions that occur in the two types of electropherogram signals considered. Given that the requisite regions are found, the subsequent solution for the unknown factor vectors can be shown to be optimal (for example, in a least mean-squares sense). Should the regions not be found, the method fails to produce a result in favor of generating an erroneous or inaccurate one. In this regard, the methods are different from classical FA or BSS that typically optimize based on general (e.g., statistical) principles that may or may not be truly characteristic of the signals being analyzed in the present context.

The processor 240 may also be configured to reduce spectral cross talk by a residual error correction ("REC") module 250. More particularly, the processor 240 can use REC module 250 to correct for spectral crosstalk by determining the residual error for a selected dye during signal amplification. In some embodiments, the residual error can be the difference between the actual signal intensity recorded and the predicted signal intensity when using the dye values generated during deconvolution. The REC module 250 can mathematically modify the pure dye matrix associated with the selected dye to reduce the residual error to become substantially flat. The pure dye matrix can be a representation of the relative signal of each dye has for each filter in the system. The processor 240 can then use the modified pure dye matrix to process the entire data set to correct for the residual error over the time course of the run.

In some embodiments, the REC module 250 can be a separate module from the processor 240. The functionality of the REC module 250 may be embodied in a computer program medium and executed by the processor 240. The REC module 250, as well as the other components of the system 200, may be implemented through hardware, software, or combinations thereof.

Figure 3:
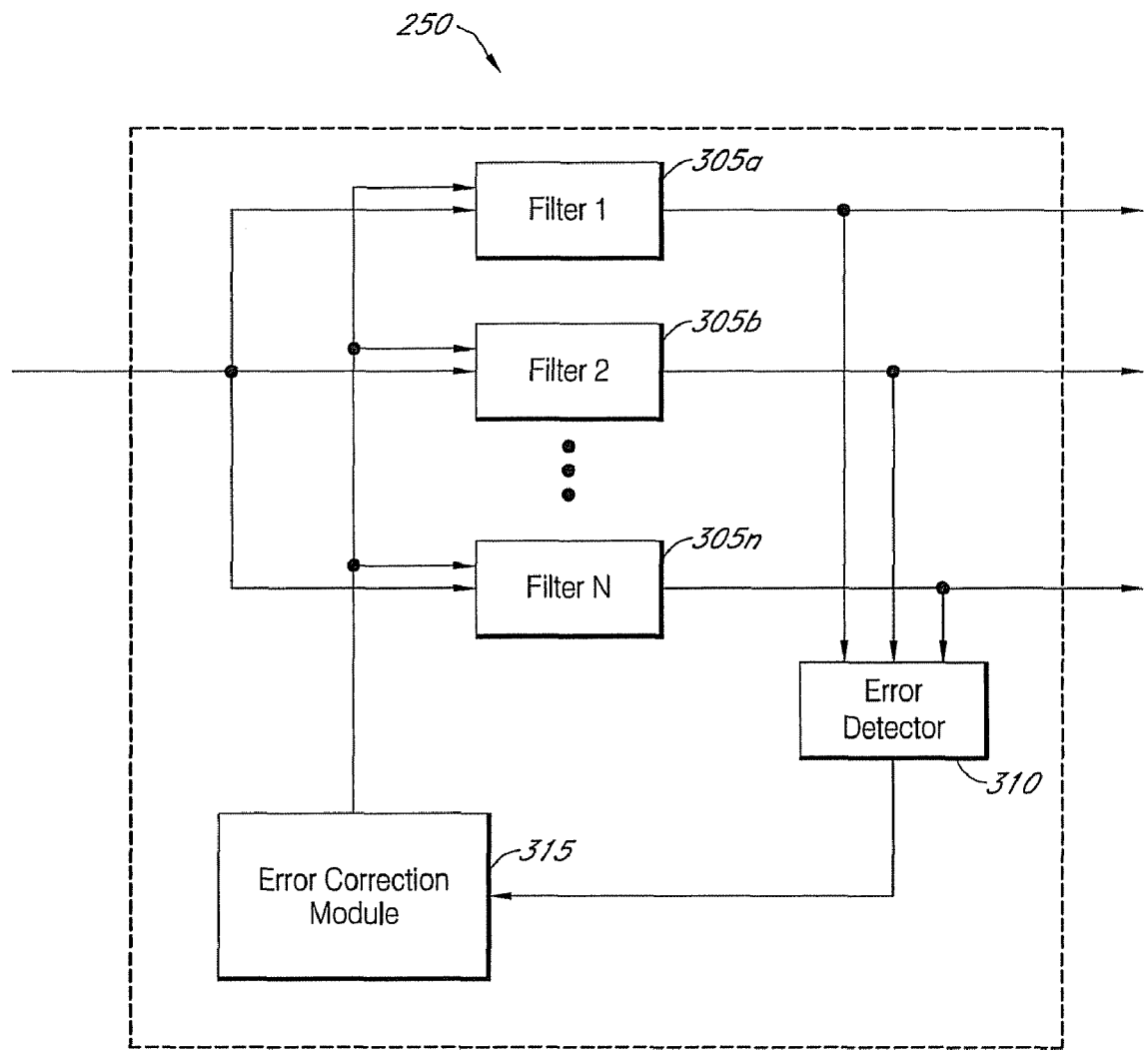
FIG. 3 illustrates a block diagram of an exemplary residual error correction module constructed according to the present teachings.

FIG. 3 illustrates a more detailed block diagram of an embodiment of the REC module 250. As shown in FIG. 3, the REC module 250 can comprise filters 305, an error detector 310, and an error correction (EC) module 315. The filters 305 can be configured for a specific frequency. For example, the VIC dye (a green fluorescent dye) produces luminescence at a particular frequency. Accordingly, filter 305b can be configured to detect that particular frequency and quantize the intensity of the frequency detected from the sample by spectral deconvolution.

Spectral deconvolution can resolve and quantize signal by solving a system of linear equations, where the equations describe the relative signal strength of each dye in all the filters. Linear algebra can then be used to solve for the relative contribution of each dye in a mixed solution. If there are more filters than unknown dyes, a regression analysis can be performed to minimize error. The remaining error is the residual that can be used to identify spectral crosstalk.

Each filter 305 can use a matrix of coefficients that is used in the spectral deconvolution of the signals from the sample. For a selected dye, the matrix of coefficients can be calibrated based on a pure form of the selected dye.

The output from the filters can be monitored by the error detector 310. The error detector 310 can be configured to determine a residual error between the pure dye response curve for each filter and the amplification spectra during dye amplification. Because the matrix for the pure dye may be affected by a variety of factors such as pH, temperature, buffer differences, dye configuration changes, and other factors, the response curve of the matrix may generate errors as compared with amplification spectra. For example, as described above for the case of VIC and Ned, a 1 nm difference between the calibration (pure dye matrix response) and the amplification spectra can lead to as much as a five percent "pull-up" or "pull-down" relative to the increasing dye. When the pure dye matrix response and the amplification spectra are identical, the residual error will remain flat during dye signal increase. If there is a slight inaccuracy in the calibration, however, the residual error will change as one dye amplifies.

Accordingly, the error correction (EC) module 315 may be configured to modify the pure dye matrix based on the received residual error. The EC module 315 can modify the coefficients in the pure dye matrix to follow the amplification spectra, i.e., where the matrix is modified so that the residual error remains flat and thus, minimizing spectral crosstalk. More particularly, the filters with the changing residual error are identified in the matrix. By examining at the actual amplification plot it is possible to determine which of the dyes has the incorrect pure calibration. The pure dye value for the dye in this filter can be modified to flatten the residual error plot. Subsequently, the signal processor 240 can use the modified pure dye matrix to process the signals from a sample. The same can be done where the REC module 250 is part of or integrated into the processor 240.

Figure 4:
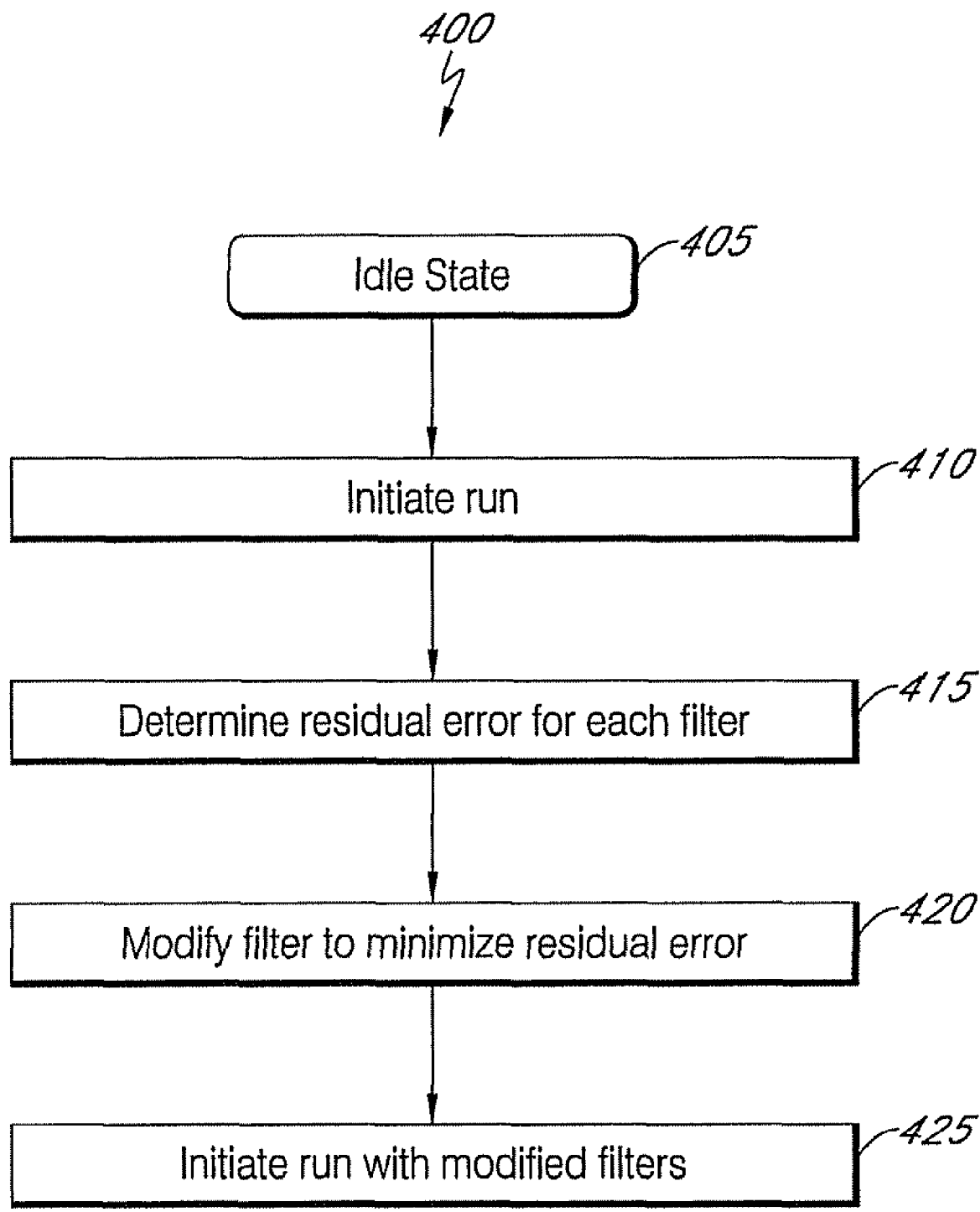
FIG. 4 illustrates a flow diagram of an embodiment according to the present teachings.

FIG. 4 illustrates a flow diagram of a system 400 implemented by yet another embodiment. It should be readily apparent to those of ordinary skill in the art that the system 400 depicted in FIG. 4 represents a generalized schematic illustration and that other steps can be added or existing steps can be removed or modified. As shown in FIG. 4, the system 400 can be in an idle state, in step 405. Once a sample is in place, the system 400 can initiate a calibration run, in step 410. More particularly, the error detector 310 can monitor and store the residual errors between the response curve of the filter associated with a selected dye and the amplification spectra during dye signal amplification.

In step 415 the residual error correction (REC) module 250 may be configured to determine the best fit error line and determine a residual error for each filter 305. In step 420, the REC module 250 may be configured to process the residual error. More specifically, the REC module 250 can modify the coefficients in the matrix of the pure dye in the associated filter 305 to follow the amplification spectra and thus, minimize the residual error. In step 425, the modified matrices may then be used to filter subsequent readings.

In some embodiments, the functionality embodied in FIG. 4 can be implemented as a computer program application. As a result, the computer program application can be invoked in response to an event, e.g., the arrival of content. In some embodiments, the functionality embodied in FIG. 4 can be implemented on a hardware platform such as an application specific integrated circuit, PROM, etc. For example, a hardware implementation of FIG. 4 can be configured to be in an idle state until invoked by a user.

In some embodiments, a system for minimizing spectral crosstalk includes a detector, a signal processor, and a residual error correction (REC) module. The detector may be configured to detect one or more signals from a sample and the signal processor may be configured to filter one or more signals. The signal processor may include one or more filters and one or more matrices. Each filter may be associated with a dye and each matrix may be associated with a respective filter. An expected response is initially configured with each matrix. The REC module may be configured to monitor for one or more residual errors of each filter during a dye amplification phase. The REC module then modifies the associated matrix of each filter to minimize the residual error.

Figure 5:
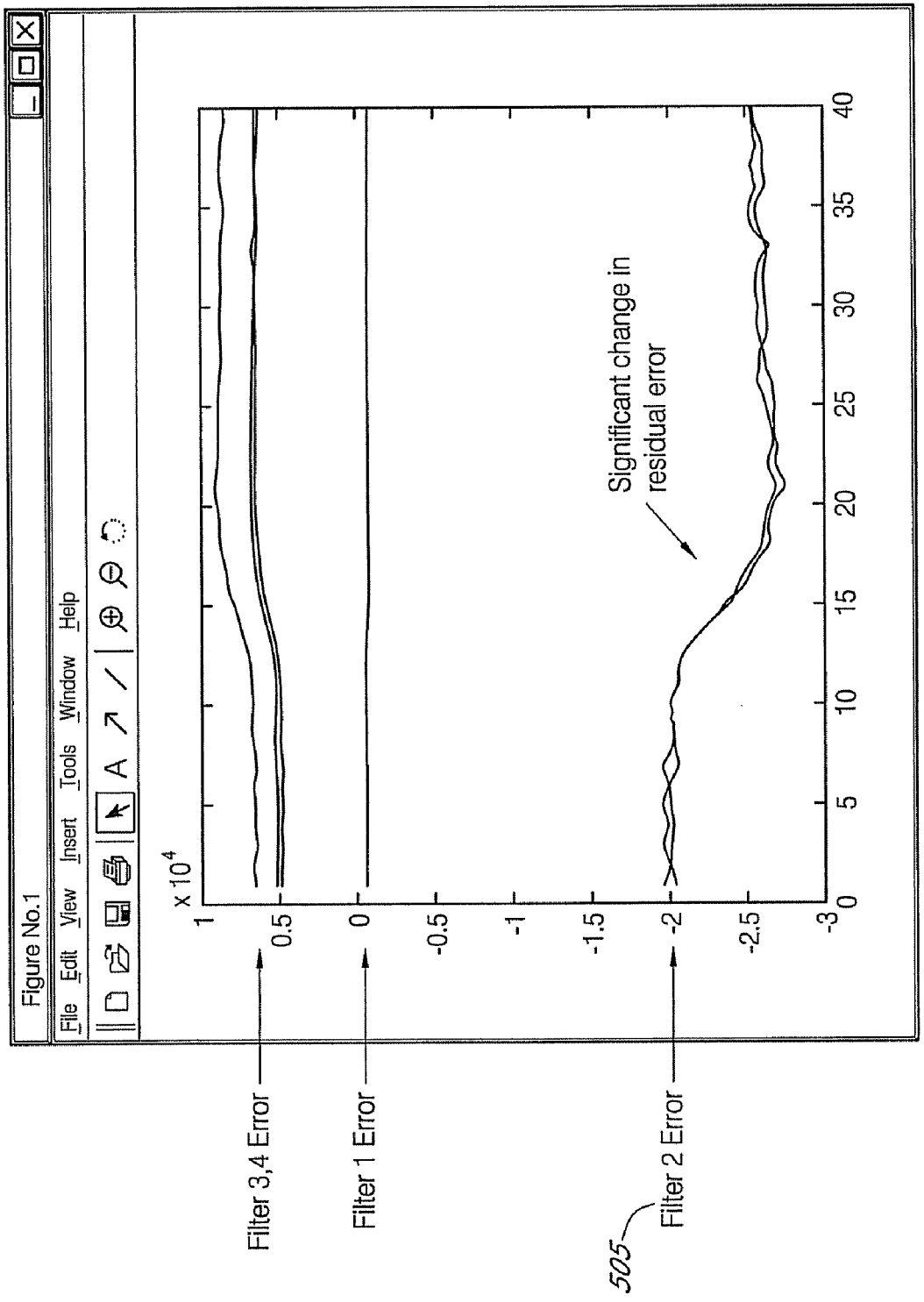
FIG. 5 illustrates exemplary residual errors for a plurality of filters.

FIG. 5 illustrates an exemplary residual error for dye 2 shown in FIG. 1 in accordance with another embodiment. As shown in FIG. 5, the Filter 2 error 505 shows a significant change in the residual error from cycles 10 to 20, which coincides with the pull-down for dye 2 in FIG. 1.

Figure 6:
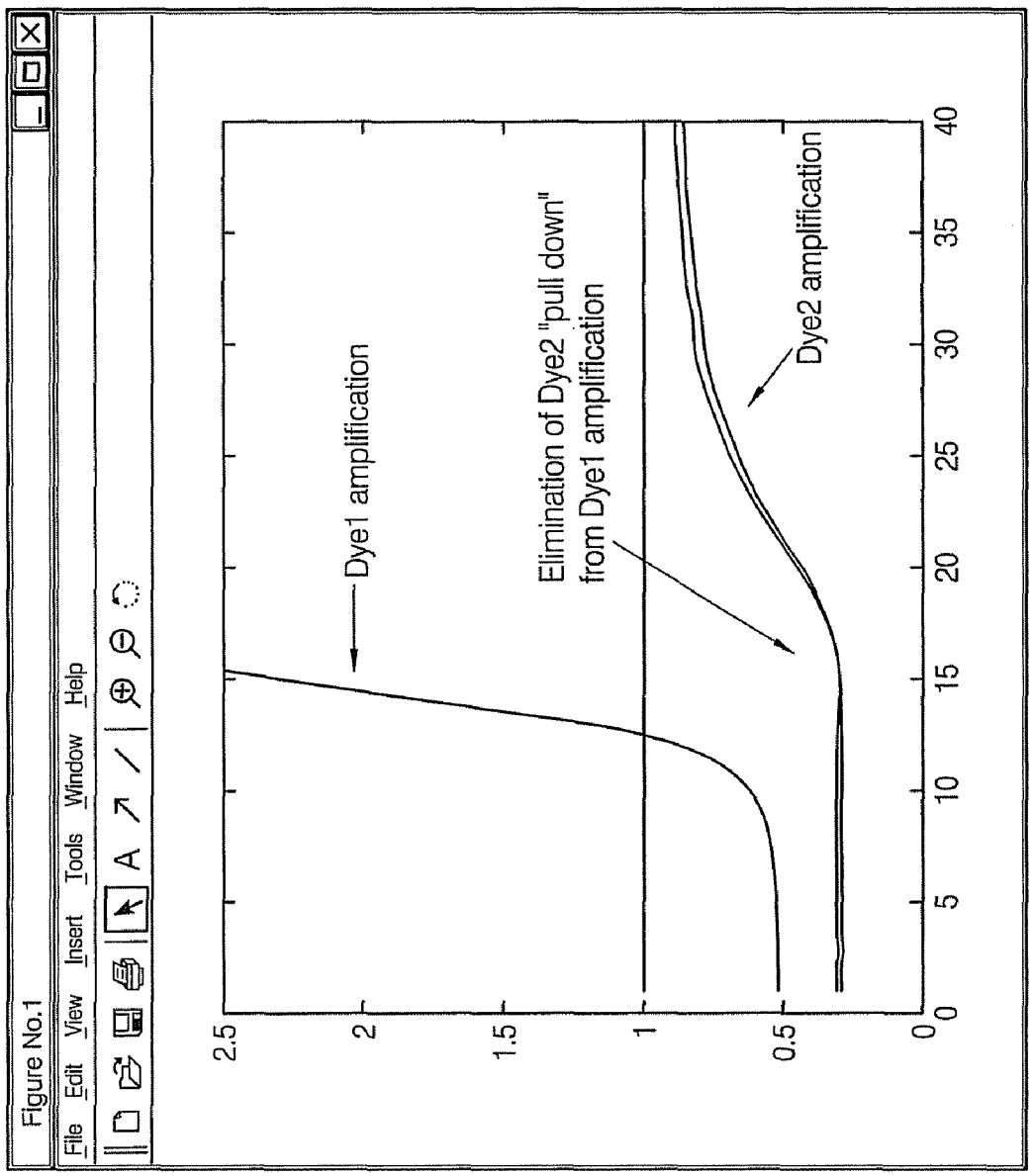
FIG. 6 illustrates exemplary amplification spectra and response curves for two dyes with the modified filters.

FIG. 6 illustrates exemplary amplification spectra and response curves for two dyes with the modified filters. As shown in FIG. 6, the amplification spectra for the dye 1 is similar to the spectra of dye 1 in FIG. 1. With the application of the REC module 250, the dye 2 amplification spectra progresses without a pull-down. From cycles 15 to 20, the amplification spectra of dye 2 does not dip but increases.

Figure 7:
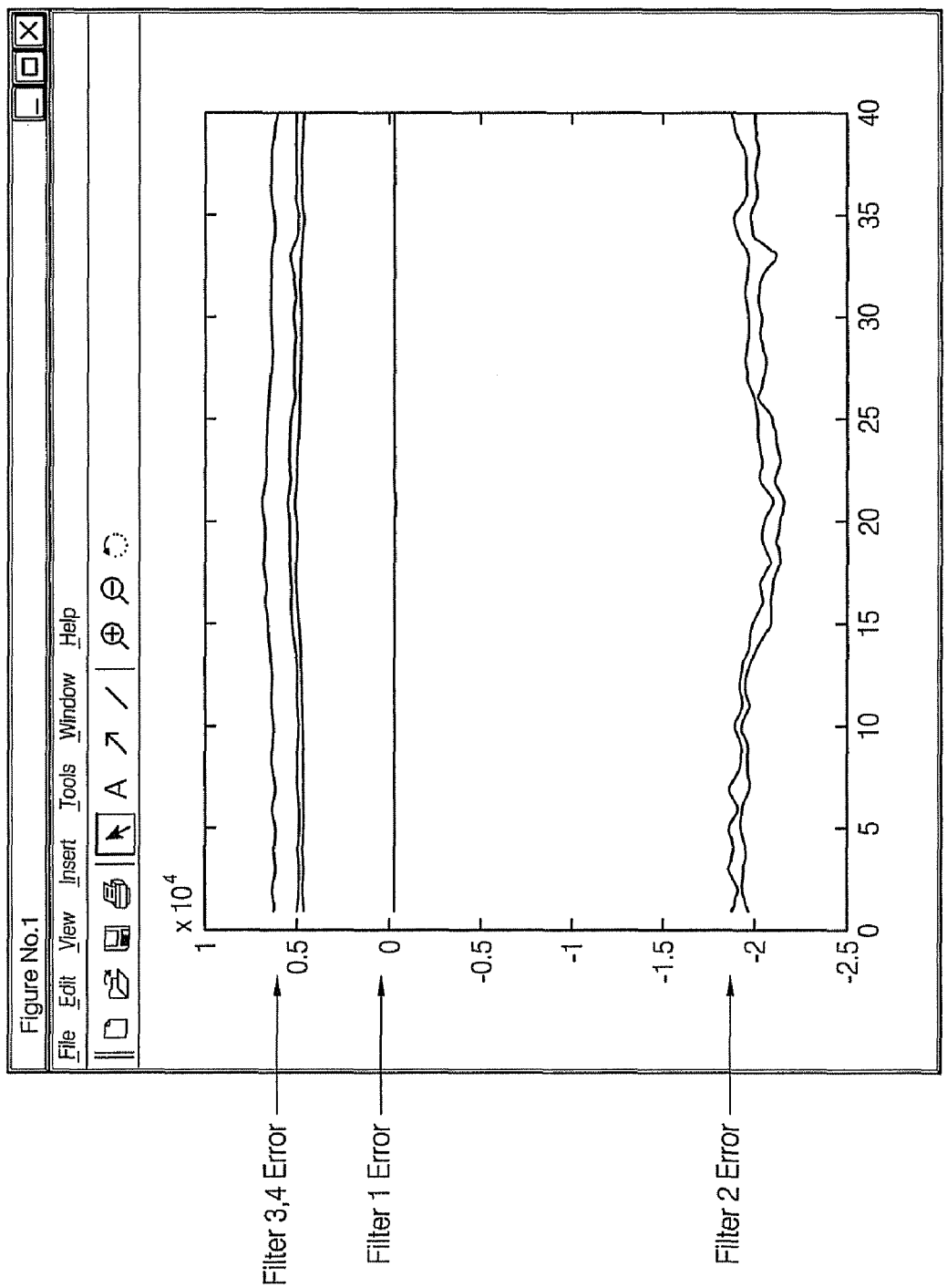
FIG. 7 illustrates exemplary residual errors for the filters with modified coefficients.

In some embodiments, the REC module modifies at least one coefficient in a matrix associated with a selected filter to thereby substantially flatten the residual error. FIG. 7 illustrates exemplary residual errors for filters with modified coefficients. The REC module may also be configured to modify one or more coefficient in a matrix associated with a selected filter to substantially mirror an amplification spectra of a dye associated with the selected filter.

FIG. 8 depicts a table of original calibration values 805 and a table of corrected calibration values 810 for the filters 305, based on exemplary data. The tables 805, 810 show values for three types of dyes: FAM, VIC, and ROX, as known to those skilled in the art. Other dyes, such as Ned and Cy5, can be used by the system 200. The rows in the tables 805, 810 represent a respective filter in the processor 240.

In some embodiments, the spectra for a dye can be affected by a variety of factors including pH, temperature, buffer differences, and changes in the dye configuration. Dyes are frequently attached to probes, including nucleic acid probes, which may affect the spectral characteristics and associated crosstalk of the dyes. Changes in spectral characteristics of an individual dye can depend on the particular probe it is attached to; for example, nucleotide sequence of the dye-probe conjugate can have particular effects. As a result, spectral shifts unique to particular dye-probe conjugates can introduce error when compared to pure dye within a calibration plate, for example. These inaccuracies can compound the error present in a dye matrix, since spectra from the same dye conjugated to different probes may not be uniform. Consequently, the response curve of the matrix will typically generate errors as compared with amplification spectra, where the resulting error can be unique to each dye-probe conjugate.

Dyes conjugated to nucleic acids may be used in real-time PCR systems to detect the presence of amplicons. As described herein, spectra from multiplexed reactions, where more than one fluorescent dye is used simultaneously, must be deconvolved to separate the contribution of each dye from the composite fluorescence measurements. Deconvolution includes a calibration step using pure-dye samples and may further include the residual error correction as already described. However, in place of or in addition to residual error correction, the error due to spectral crosstalk and the "pull up" or "pull down" for a particular dye-probe conjugate can be reduced based on the sequence identity of a nucleic acid conjugated to a dye.

Figure 9:
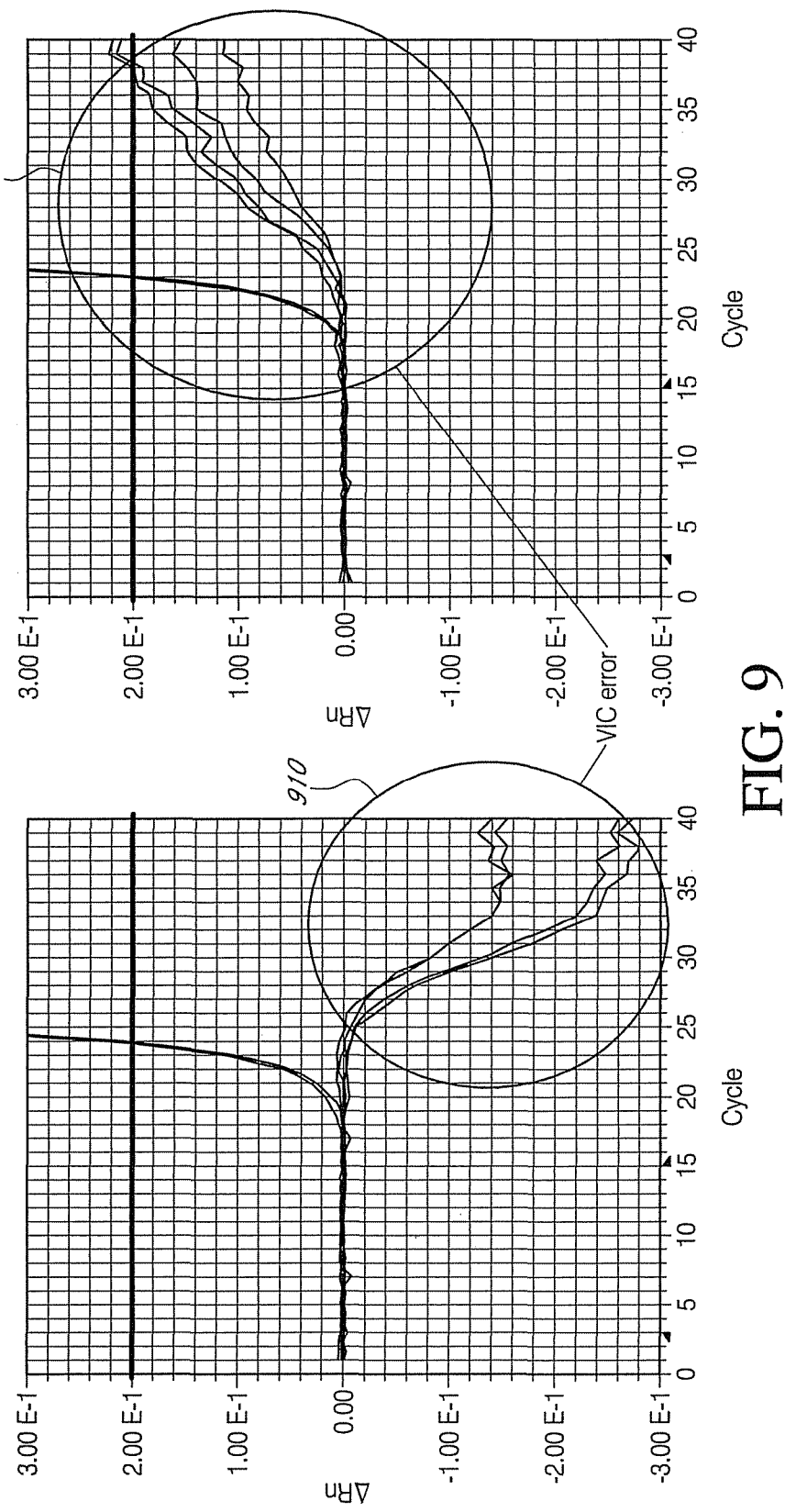
FIG. 9A illustrates exemplary amplification spectra where multicomponenting error is negative due to a particular dye-nucleotide conjugation.
FIG. 9B illustrates exemplary amplification spectra where multicomponenting error is positive due to a particular dye-nucleotide conjugation.

FIGS. 9A and 9B illustrate amplification spectra where multicomponenting error is negative 910 or positive 920, respectively, due to particular dye-nucleotide conjugation.

Figure 10:
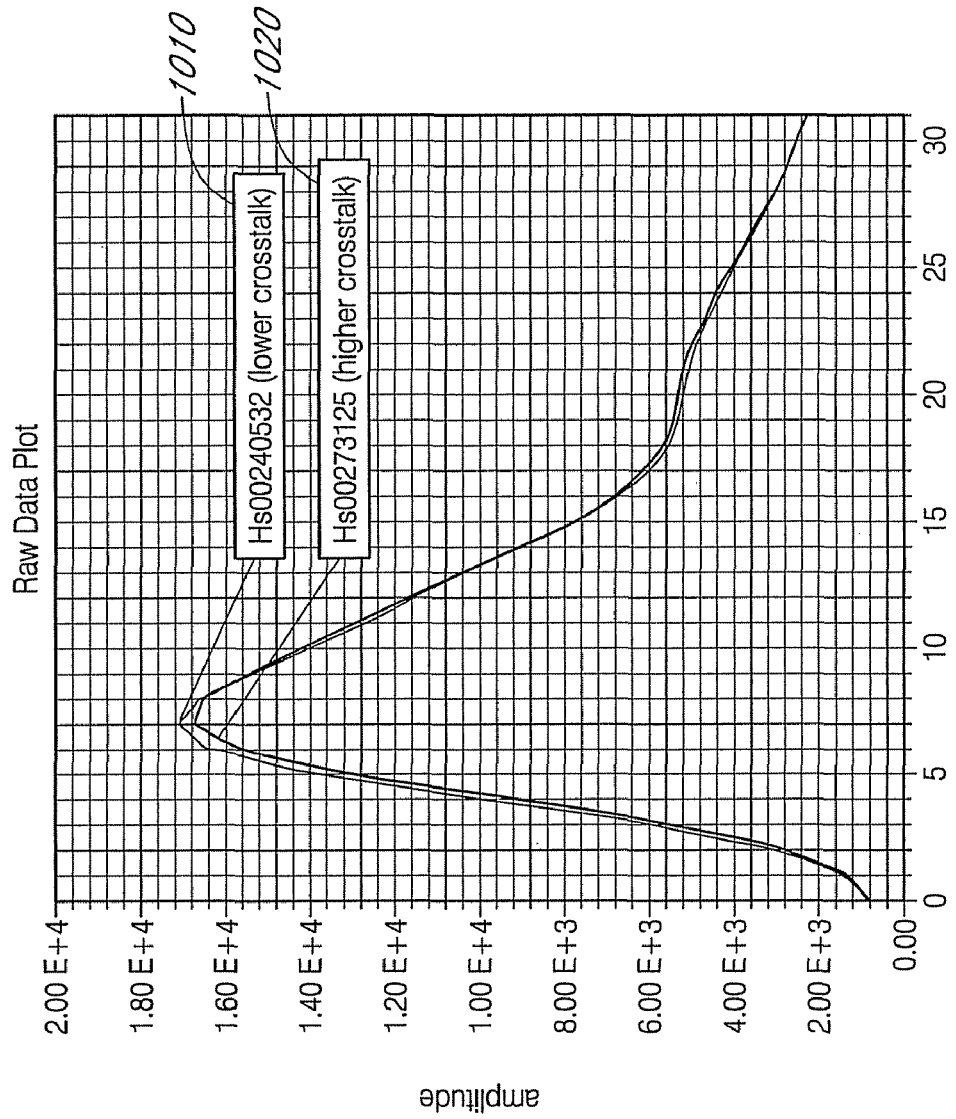
FIG. 10 illustrates an exemplary spectral shift based on a dye conjugated to two different probes.

FIG. 10 illustrates an exemplary spectral shift based on a dye conjugated to two probes of different nucleotide sequence. Probe sequence may elicit lower crosstalk 1010 or higher crosstalk 1020 for a particular dye.

In some embodiments, a compensated correction based on a particular dye-probe conjugate can be determined a priori and applied to consecutive experimental measurements. The relative spectral shift between the dye-probe conjugate and pure dye is calculated, with the magnitude and direction of the shift recorded for each particular dye-probe conjugate to be used in a multiplexed reaction. These probe specific correction values can then be stored and/or applied to subsequent experimental measurements. These probe specific correction values may also be incorporated into the residual error correction and/or used by the REC module to modify one or more filters. The correction value for a particular dye-probe conjugate can be included as part of an algorithm and can be stored and retrieved for use in subsequent assays employing that conjugate.

Signals may be processed, therefore, by a method that includes a first dye signal based on measurement of a first dye and at least one probe signal based on measurement of the first dye conjugated to a first probe. The change between the first dye signal and the probe signal can be processed to provide a first correction value that is particular to the first dye conjugated to the first probe. Such a method may also include deconvoluting a multiplexed signal using the first correction value, where the multiplexed signal has a component from the first probe. In some cases, the probe signal based on measurement of the first dye conjugated to a first probe includes a plurality of probe signals each based on measurement of said first dye conjugated to a plurality of different probes. Furthermore, the change between the first dye signal and each of the plurality of probe signals can be processed to provide a plurality of correction values particular to the first dye conjugated to each respective probe. Likewise, methods can further include second dye signals and second probes that are processed in similar manners. When two or more dyes are used, the methods may further include deconvoluting a multiplexed signal that includes components from each probe using correction values unique to each.

In some embodiments, instrument or system specific correction values can be determined for a particular dye-probe conjugate. Dyes conjugated to particular nucleotide sequences may be used in the calibration plates so that deconvolution of dye spectra accounts for the probe sequence identity in addition to particular assay or reaction conditions such as pH, temperature, and buffer differences. For example, a calibration plate containing sets of dye-probe conjugates may be used to account for probe-specific spectral shifts. The calibration values can then be stored in the specific instrument or system to provide correction values unique to that specific instrument or system. These values may then be retrieved for subsequent processing of assays utilizing the corresponding dye-probe conjugates. Alternatively, the calibration plate containing the dye-probe conjugates can be used to calibrate the instrument or system each time an experiment is run.

In some embodiments, one or more correction values for particular dye-probe conjugates are used in methods for correcting spectral shift based on a particular dye-probe conjugation. For example, probe measurements may be acquired later in time that are corrected using one or more correction values determined previously using methods of the present teachings. Various instruments, hardware, software, and systems may include and apply such previously determined correction values. Or, in some cases, some or all of the necessary correction values may be determined de novo according to the present methods.

In some embodiments, the calibration plate including particular dye-probe conjugates can be used in conjunction with methods and systems employing residual error correction. Optimized calibration corrections may be generated for categories of multiplexed assays or reactions that share probe characteristics such as nucleic acid sequence. For example, a calibration plate can be used that includes a particular dye conjugated to each possible nucleotide or dinucleotide sequence, where each dye-nucleotide conjugation causes unique spectral shifts in comparison to pure dye. The dye-probe conjugates may comprise nucleotide sequence that includes, but is not limited to, the following nucleotides: adenosine (A), cytosine (C), guanosine (G), thymidine (T), uridine (U), and inosine (I), including both the ribo- and deoxyribo-variants thereof.

In some embodiments, the present teachings are applicable to processing signals from multiplexed real-time PCR reactions, including reactions based on the TaqMan® probes (Applied Biosystems, Foster City, Calif.). The quality of the spectral deconvolution can vary between assays, and can vary with the 5' terminal nucleotide sequence of the dye-probe conjugate (e.g., a TaqMan® probe). Although not wishing to be bound by theory, it is possible that the mechanism for assay-specific spectral deconvolution error may be due to spectral shifts of the dye fluorescence caused by linkage of the dye to nucleotides that are cleaved along with the dye in the 5' nuclease reaction. In particular, the sequence identity of one or more nucleotides closest to the conjugated dye may affect the dye spectrum. In some cases, the dye may be conjugated to the 5' end of the nucleic acid probe. As an example, a dye-probe conjugate whose 5' nucleotide sequence is A can have an emission spectrum shifted a few nanometers longer than a probe with a 5' nucleotide sequence of C. Differences can exist for dinucleotide sequences, e.g., AA compared to AC, or trinucleotide sequences and so on. The emission spectrum difference manifests itself as error in the deconvolved dye signals, which are proportional to the magnitude of the composite fluorescence measurements.

In various embodiments, the dye includes a fluorescent dye, a poly-nucleotide specific dye, a phosphorescent dye, or a chemiluminescent dye.

The fluorescent dye may include VIC, Ned, FAM, ROX, Cy5, fluorescein, 6-FAM, rhodamine, Texas Red, tetramethylrhodamine, a carboxyrhodamine, carboxyrhodamine 6G, carboxyrhodol, carboxyrhodamine 110, Cascade Blue, Cascade Yellow, coumarin, Cy2, Cy3, Cy3.5, Cy5, Cy5.50, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, 7-amino-4-methylcoumarin-3-acetic acid, BODIPY FL, BODIPY FL-Br sub.2, BODIPY 530/550, BODIPY 558/568, BODIPY 564/570, BODIPY 576/589, BODIPY 581/591, BODIPY 630/650, BODIPY 650/665, BODIPY R6G, BODIPY TMR, BODIPY TR, conjugates thereof, and combinations thereof.

The polynucleotide-specific dye may include acridine orange, acridine homodimer, actinomycin D, 7-aminoactinomycin D (7-AAD), 9-amino-6-chloro-2-methoxyacridine (ACMA), BOBO-1 iodide (462/481), BOBO-3 iodide (570/602), BO-PRO-1 iodide (462/481), BO-PRO-3 iodide (575/599), 4',6-diamidino-2-phenylindole, dihydrochloride (DAPI), 4',6-diamidino-2-phenylindole, dihydrochloride (DAPI), 4',6-diamidino-2-phenylindole, dilactate (DAPI, dilactate), dihydroethidium(hydroethidine), dihydroethidium(hydroethidine), dihydroethidium(hydroethidine), ethidium bromide, ethidium diazide chloride, ethidium homodimer-1 (EthD-1), ethidium homodimer-2 (EthD-2), ethidium monoazide bromide (EMA), hexidium iodide, Hoechst 33258, Hoechst 33342, Hoechst 34580, Hoechst S769121, hydroxystilbamidine, methanesulfonate, JOJO-1 iodide (529/545), JO-PRO-1 iodide (530/546), LOLO-1 iodide (565/579), LO-PRO-1 iodide (567/580), NeuroTrace 435/455, NeuroTrace 500/525, NeuroTrace 515/535, NeuroTrace 530/615, NeuroTrace 640/660, OliGreen, PicoGreen ssDNA, PicoGreen dsDNA, POPO.TM.-1 iodide (434/456), POPO.TM.-3 iodide (534/570), PO-PRO.TM.-1 iodide (435/455), PO-PRO.TM.-3 iodide (539/567), propidium iodide, RiboGreen, SlowFade, SlowFade Light, SYBR Green I, SYBR Green II, SYBR Gold, SYBR 101, SYBR 102, SYBR 103, SYBR DX, TO-PRO-1, TO-PRO-3, TO-PRO-5, TOTO-1, TOTO-3, YO-PRO-1 (oxazole yellow), YO-PRO-3, YOYO-1, YOYO-3, TO, SYTOX Blue, SYTOX Green, SYTOX Orange, SYTO 9, SYTO BC, SYTO 40, SYTO 41, SYTO 42, SYTO 43, SYTO 44, SYTO 45, SYTO Blue, SYTO 11, SYTO 12, SYTO 13, SYTO 14, SYTO 15, SYTO 16, SYTO 20, SYTO 21, SYTO 22, SYTO 23, SYTO 24, SYTO 25, SYTO Green, SYTO 80, SYTO 81, SYTO 82, SYTO 83, SYTO 84, SYTO 85, SYTO Orange, SYTO 17, SYTO 59, SYTO 60, SYTO 61, SYTO 62, SYTO 63, SYTO 64, SYTO Red, netropsin, distamycin, acridine orange, 3,4-benzopyrene, thiazole orange, TOMEHE, daunomycin, acridine, pentyl-TOTAB, and butyl-TOTIN, conjugates thereof, and combinations thereof. Asymmetric cyanine dyes may be used as the polynucleotide-specific dye. Other dyes of interest include those described by Geierstanger, B. H. and Wemmer, D. E., Annu. Rev. Vioshys. Biomol. Struct. 1995, 24, 463-493, by Larson, C. J and Verdine, G. L., Bioorganic Chemistry: Nucleic Acids, Hecht, S. M., Ed., Oxford University Press: New York, 1996; pp 324-346, and by Glumoff, T. and Goldman, A. Nucleic Acids in Chemistry and Biology, 2nd ed., Blackburn, G. M. and Gait, M. J., Eds., Oxford University Press: Oxford, 1996, pp 375-441. The polynucleotide-specific dye may be an intercalating dye, and may be specific for single stranded polynucleotides or specific for double-stranded polynucleotides.

Chemiluminescent dyes may include N-(4-Aminobutyl)-N-ethylisoluminol, Luminol, 4-Aminophthalhydrazide monohydrate, Bis(2-carbopentyloxy-3,5,6-trichlorophenyl) oxalate, 9,10-Bis(phenylethynyl)anthracene, 5,12-Bis(phenylethynyl)naphthacene, 2-Chloro-9,10-bis(phenylethynyl) anthracene, 1,8-Dichloro-9,10-bis(phenylethynyl) anthracene, Lucifer Yellow CH dipotassium salt, Lucifer yellow VS dilithium salt, 2,4,5-Triphenylimidazole, 9,10-Diphenylanthracene, 97%, Rubrene, Tetrakis(dimethylamino)ethylene, conjugates thereof, and combinations thereof.

Other dyes and fluorophores are described at www.probes.com (Molecular Probes, Inc.).

Figure 11:
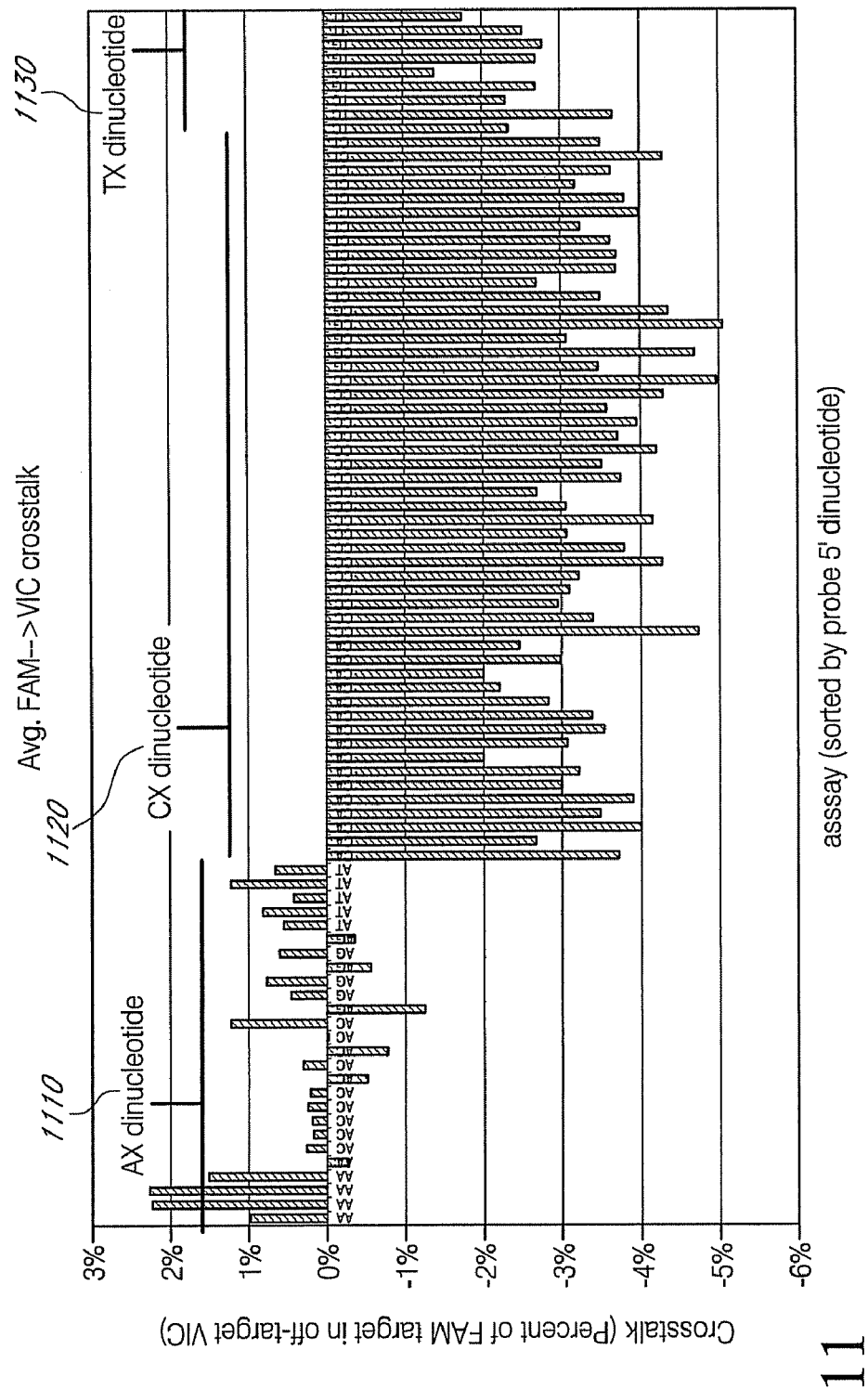
FIG. 11 illustrates exemplary crosstalk values between two dyes based on various dinucleotide conjugations.

FIG. 11 illustrates exemplary crosstalk values between dyes based on various dinucleotide conjugations. The exemplary data is based on 96 PCR assays with the FAM dye conjugated to the indicated dinucleotide shown on the x-axis labels. The various dinucleotide sequences of the probes are sorted by AX 1110, CX 1120, and TX 1130, where X may be A, C, G, or T as further indicated on the x-axis.

In some embodiments, the present teachings can be performed as one or more computer programs. The computer program can exist in a variety of forms both active and inactive. For example, the computer program can exist as software program(s) comprised of program instructions in source code, object code, executable code or other formats; firmware program(s); or hardware description language (HDL) files. Any of the above can be embodied on a computer readable medium, which include storage devices and signals, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes. Exemplary computer readable signals, whether modulated using a carrier or not, are signals that a computer system hosting or running the present teachings can be configured to access, including signals downloaded through the Internet or other networks. Concrete examples of the foregoing include distribution of executable software program(s) of the computer program on a CD-ROM or via Internet download. In a sense, the Internet itself, as an abstract entity, is a computer readable medium. The same is true of computer networks in general.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

What is claimed is:

1. A method for processing signals, the method comprising:
    providing a first dye signal based on measurement of a first dye;
    providing at least one probe signal based on measurement of said first dye conjugated to a first probe; and
    processing a change between said first dye signal and said at least one probe signal to provide a first correction value particular to said first dye conjugated to said first probe.

2. The method according to claim 1, further comprising:
    deconvoluting a multiplexed signal that includes a component from said first probe using said first correction value.

3. A method of claim 1, wherein said first probe is a nucleic acid.

4. A method of claim 1, wherein providing at least one probe signal based on measurement of said first dye conjugated to a first probe comprises:
    providing a plurality of probe signals each based on measurement of said first dye conjugated to a plurality of different probes; and
    wherein processing the change between said first dye signal and said at least one probe signal to provide a first correction value particular to said first dye conjugated to said first probe comprises:
    processing the change between said first dye signal and each of said plurality of probe signals to provide a plurality of correction values particular to said first dye conjugated to each respective probe.

5. A method of claim 4, wherein said plurality of different probes comprises:
    a plurality of nucleic acids each conjugated with said first dye.

6. A method of claim 5, wherein said plurality of nucleic acids each conjugated with said first dye includes at least one nucleic acid conjugated via a nucleotide selected from the group consisting of A, C, G, U, I, dA, dC, dG, dT, dI.

7. A method of claim 5, wherein said plurality of nucleic acids each conjugated with said first dye includes at least one nucleic acid conjugated via a dinucleotide having a sequence NN, where each N is a nucleotide selected from the group consisting of A, C, G, U, I, dA, dC, dG, dT, dI.

8. A method of claim 1, further comprising:
providing a second dye signal based on measurement of a second dye;
providing a second probe signal based on measurement of said second dye conjugated to a second probe; and
processing the change between said second dye signal and said second probe signal to provide a second correction value particular to said second dye conjugated to said second probe.

9. A method of claim 8, further comprising:
deconvoluting a multiplexed signal that includes components from said first and second probes, wherein deconvoluting uses at least one of said first and second correction values.

10. A method for correcting spectral shift based on dye-probe conjugation comprising:
adjusting a probe measurement using a first correction value as determined by the method of claim 1.

11. A method for correcting spectral shift based on dye-probe conjugation comprising:
deconvoluting a multiplexed probe measurement, said multiplexed probe measurement including a component from a first probe, and said deconvoluting using at least a first correction value determined by the method of claim 1.

12. A method for correcting spectral shift based on dye-probe conjugation comprising:
deconvoluting a multiplexed probe measurement, wherein said multiplexed probe measurement includes components from a plurality of different probes, wherein deconvoluting uses a plurality of correction values determined by the method of claim 4.

13. An apparatus comprising means for performing the method of claim 10.

14. An apparatus comprising means for performing the method of claim 11.

15. An apparatus comprising means for performing the method of claim 12.

16. A computer-readable medium comprising computer-executable instructions for peforming the method of claim 10.

17. A computer-readable medium comprising computer-executable instructions for peforming the method of claim 11.

18. A computer-readable medium comprising computer-executable instructions for performing the method of claim 12.

19. A method for processing signals, the method comprising:
providing a plurality of filters, each filter configured to process an associated dye;
determining a residual error for at least one filter during dye amplification;
modifying said at least one filter based on said residual error and based on a first correction value, where said first correction value is determined by the method of claim 1; and
filtering subsequent signals associated with the modified at least one filter.

20. A method of claim 19, wherein the step of determining a residual error further comprises:
monitoring a response curve of said at least one filter for a selected sample; and
determining at least one error between said response curve and an expected response curve for said at least one filter.

21. A method of claim 20, further comprising:
modifying coefficients of a matrix associated with said at least one filter to substantially minimize said residual error.

22. An apparatus comprising means for performing the method of claim 19.

23. A computer-readable medium comprising computer-executable instructions for performing the method of claim 19.

24. A system for minimizing spectral crosstalk, the system comprising:
a detector configured to detect a plurality of signals from a sample;
a signal processor configured to filter said plurality of signals, wherein said signal processor comprises:
a plurality of filters, each filter associated with a dye;
a plurality of matrices, each matrix associated with a respective filter, wherein each matrix is initially configured with an expected response;
a plurality of correction values, wherein each of said correction values is determined by the method of claim 1; and
a residual error correction ("REC") module configured to monitor for residual errors of said plurality of filters during a dye amplification phase and to modify said associated matrices of said plurality of filters to minimize said residual errors.

25. A system of claim 24, wherein said REC module is further configured to modify at least one coefficient in a matrix associated with a selected filter to substantially minimize said residual error.

26. A system of claim 24, wherein said REC module is further configured to modify at least one coefficient in a matrix associated with a selected filter to substantially mirror an amplification spectra of a dye associated with said selected filter.

27. A system of claim 24, wherein said dye is one of VIC, Ned, FAM, ROX, and Cy5.

28. A system of claim 24, wherein said REC module is further configured to perform a least squares fit in response to said residual error generating more equations than unknowns.

29. A system for minimizing spectral crosstalk, the system comprising:
a detector configured to detect a plurality of signals from a sample;
a signal processor configured to filter the plurality of signals, wherein the signal processor comprises:
a plurality of filters each associated with a dye;
a plurality of matrices each associated with a respective filter, each matrix being initially configured with an expected response; and
a residual error correction ("REC") module configured to monitor for residual errors of the plurality of filters during a dye amplification phase and to modify at least one of the plurality of matrices to minimize the residual error.

30. The system according to claim 29, wherein the REC module is further configured to modify at least one coefficient in the matrix associated with a selected filter to substantially minimize the residual error.

31. The system according to claim 29, wherein the REC module is further configured to modify at least one coefficient in a matrix associated with a selected filter to substantially mirror an amplification spectra of a dye associated with the selected filter.

32. The system according to claim 29, wherein the dye is one of VIC, Ned, FAM, ROX, and Cy5.

33. The system according to claim 29, wherein the REC module is further configured to perform a least squares fit in response to the residual error generating more equations than unknowns.

\* \* \* \* \*